United States Patent
Kamakura et al.

(10) Patent No.: US 9,205,060 B2
(45) Date of Patent: Dec. 8, 2015

(54) ADHESIVE SKIN PATCH CONTAINING SEROTONIN RECEPTOR ANTAGONIST DRUG

(75) Inventors: Takashi Kamakura, Higashikagawa (JP); Daiki Takano, Higashikagawa (JP)

(73) Assignee: Teikoku Seiyaku Co., Ltd., Kagawa (JP)

(*) Notice: Subject to any disclaimer, the term of this patent is extended or adjusted under 35 U.S.C. 154(b) by 5 days.

(21) Appl. No.: 14/130,385

(22) PCT Filed: Jul. 4, 2012

(86) PCT No.: PCT/JP2012/067052
§ 371 (c)(1),
(2), (4) Date: Mar. 10, 2014

(87) PCT Pub. No.: WO2013/005760
PCT Pub. Date: Jan. 10, 2013

(65) Prior Publication Data
US 2014/0179734 A1    Jun. 26, 2014

(30) Foreign Application Priority Data
Jul. 7, 2011  (JP) ................. 2011-150778

(51) Int. Cl.
| A61K 9/70 | (2006.01) |
| A61K 47/14 | (2006.01) |
| A61K 47/18 | (2006.01) |
| A61K 47/32 | (2006.01) |

(Continued)

(52) U.S. Cl.
CPC .............. *A61K 9/7061* (2013.01); *A61K 9/70* (2013.01); *A61K 31/4178* (2013.01); *A61K 31/4184* (2013.01); *A61K 31/439* (2013.01); *A61K 47/14* (2013.01); *A61K 47/18* (2013.01); *A61K 47/32* (2013.01)

(58) Field of Classification Search
None
See application file for complete search history.

(56) References Cited

U.S. PATENT DOCUMENTS

| 5,830,497 A | 11/1998 | Yamanaka et al. |
| 8,246,981 B2 * | 8/2012 | Patel et al. ............ 424/449 |

(Continued)

FOREIGN PATENT DOCUMENTS

| CN | 102293761 | 12/2011 |
| JP | 2-255612 | 10/1990 |

(Continued)

OTHER PUBLICATIONS

Supplementary European Search Report (ESR) issued Nov. 21, 2014 in corresponding European Patent Application No. EP 12 80 8108.

(Continued)

*Primary Examiner* — Robert A Wax
*Assistant Examiner* — Melissa Mercier
(74) *Attorney, Agent, or Firm* — Wenderoth, Lind & Ponack, L.L.P.

(57) ABSTRACT

Provided is a transdermal absorption-type patch containing a serotonin receptor antagonist, which has a short transdermal absorption delay time (lag time), and in which the maximum transdermal permeation rate of the drug can be reached within a short time and the drug can disappear from circulating blood rapidly. That is, provided is a patch containing a serotonin receptor antagonist, wherein the patch contains an adhesive layer comprising a non-functional acrylic adhesive, a water-soluble organic amine, a fatty acid ester, and a serotonin receptor antagonist such as granisetron as an active ingredient.

10 Claims, 1 Drawing Sheet

(51) Int. Cl.
*A61K 31/4178* (2006.01)
*A61K 31/4184* (2006.01)
*A61K 31/439* (2006.01)

(56) References Cited

U.S. PATENT DOCUMENTS

| | | |
|---|---|---|
| 2006/0263421 A1 | 11/2006 | Patel et al. |
| 2007/0264319 A1 | 11/2007 | Lebo et al. |
| 2008/0262445 A1 | 10/2008 | Hsu et al. |
| 2009/0285877 A1 | 11/2009 | Yasukochi et al. |

FOREIGN PATENT DOCUMENTS

| | | | |
|---|---|---|---|
| JP | 8-34731 | | 2/1996 |
| JP | 9-169636 | | 6/1997 |
| JP | 9-278651 | | 10/1997 |
| JP | H09278651 | * | 10/1997 |
| JP | 2002-332228 | | 11/2002 |
| JP | 2005-170833 | | 6/2005 |
| JP | 2006-516601 | | 7/2006 |
| JP | 2008-511663 | | 4/2008 |
| JP | 2008-512471 | | 4/2008 |
| JP | 2008-540662 | | 11/2008 |
| JP | 2009-137925 | | 6/2009 |
| JP | 2009137925 | * | 6/2009 |
| WO | 2004/069141 | | 8/2004 |
| WO | 2006/028863 | | 3/2006 |
| WO | 2006/029192 | | 3/2006 |
| WO | 2006/124807 | | 11/2006 |
| WO | 2009/139411 | | 11/2009 |

OTHER PUBLICATIONS

International Search Report (ISR) issued Aug. 14, 2012 in International (PCT) Application No. PCT/JP2012/067052.
English translation of International Preliminary Report on Patentability issued Jan. 16, 2014 in International (PCT) Application No. PCT/JP2012/067052.

* cited by examiner

ADHESIVE SKIN PATCH CONTAINING SEROTONIN RECEPTOR ANTAGONIST DRUG

TECHNICAL FIELD

The present invention relates to a transdermal absorption-type patch which enables efficient and continuous absorption of a serotonin receptor antagonist used as a therapeutic drug for nausea and vomiting from a skin as an active ingredient, is used for the prevention and treatment of nausea and vomiting at the time of cancer chemotherapy, and can be administered once daily.

BACKGROUND ART

Symptoms such as nausea and vomiting are considered to appear at the time of cancer chemotherapy with a probability of about 70-80%. Because the persistent nausea and vomiting cause dehydration, electrolyte abnormality or undernutrition, a patient feels strong physiological and psychological discomfort resulting in great distress in the patient. Therefore, it is the top priority in clinical practice to minimize nausea and vomiting.

As a therapeutic drug which suppresses these symptoms such as nausea and vomiting, a serotonin receptor antagonist such as granisetron hydrochloride, ramosetron hydrochloride, or ondansetron hydrochloride is generally and widely used in clinical practice.

As an administration method of said serotonin receptor antagonist, oral administration or intravenous administration is generally carried out. However, because it is not easy to administer an oral drug to a patient who suffers from nausea and vomiting or has difficulty in swallowing, and even when administered, there is a possibility that the patient spits up the drug, an oral administration is not preferable in light of QOL (Quality of Life) of the patient.

Also, regarding intravenous injection, it causes pain to a patient, and has restrictions such as the impossibility of applying to a patient who receives home medical care because it requires treatment by a medical doctor or a nurse. Therefore, the intravenous injection is also not preferable in light of QOL (Quality of Life) of the patient.

Thus, a variety of attempts have been made to develop a transdermal absorption-type patch which can be easily administered to a patient, does not cause pain to the patient, and thereby could improve QOL (Quality of Life) of the patient.

As the above transdermal absorption-type patch, an adhesive patch which comprises an acrylic adhesive containing a non-acidic hydroxyl moiety and filled with a physiologically effective amount of granisetron (Patent Document 1), and a patch which comprises an adhesive containing a serotonin receptor antagonist in an effective amount for antiemetic activity and an absorption enhancer, and can be applied to a skin for 24 hours or more (Patent Document 2), have been developed.

However, regarding the formulation in Patent Document 1, because it is prepared by using a hydroxyl group as a functional group in the acrylic adhesive so that the formulation can be applied to a skin for a long time (24 hours or more), there are problems such as too strong initial adhesive power and holding power, resulting in a peeling of a horny layer simultaneously with a peeling of the formulation, which causes a strong skin irritation. Also, because of the presence of a functional group in the adhesive, the transdermal absorbability is also insufficient.

Furthermore, Patent Document 3 discloses a transdermal absorption-tape containing granisetron in an adhesive base consisting of a copolymer of 2-ethylhexyl acrylate and vinylpyrrolidone, isopropyl myristate, and lauric acid diethanolamide. Although said formulation is characterized in that it can continuously release a drug, there is still scope for improvement in view of the rapid onset of drug efficacy required for a formulation for once-daily administration. Also, because said formulation contains lauric acid diethanolamide, which is a non-ionic surfactant, it causes a strong skin irritation.

RELATED ART DOCUMENTS

Patent Documents

Patent Document 1: JP 2006-516601 A
Patent Document 2: JP 2008-540662 A
Patent Document 3: JP 2009-137925 A

SUMMARY OF THE INVENTION

Problems to be Solved by the Invention

As stated above, although attempts have been made until now to develop a transdermal absorption-type patch containing a serotonin receptor antagonist which can be easily administered to a patient, does not cause pain to the patient, and thereby could improve QOL (Quality of Life) of the patient, a transdermal absorption-type patch having properties required for a formulation for once-daily administration, i.e., a rapid onset of drug efficacy, a sufficient transdermal absorbability of the drug, and a rapid drug elimination from circulating blood, has not been developed so far.

Accordingly, an object of the present invention is to provide a transdermal absorption-type patch containing a serotonin receptor antagonist which has a short transdermal absorption delay time (lag time), and in which the maximum transdermal permeation rate of the drug (maximum flux: $\mu g/cm^2/hr$) can be reached within a short time, i.e., the onset of maximum drug efficacy is rapidly achieved.

Also, another object of the present invention is to provide a transdermal absorption-type patch containing a serotonin receptor antagonist in which the drug disappears from circulating blood rapidly, which is suitable for once-daily application.

Means for Solving the Problems

The present inventors have studied earnestly, found that a novel patch containing a serotonin receptor antagonist which has a significantly shorter transdermal absorption delay time (lag time) compared to a conventional patch for transdermal absorption containing a serotonin receptor antagonist, achieves the maximum transdermal permeation rate of the drug within a short time, shows a rapid onset of drug efficacy, shows a sufficient transdermal absorbability, and shows a rapid drug elimination from circulating blood, can be provided by preparing a patch containing an adhesive layer comprising a non-functional acrylic adhesive, a water-soluble organic amine, a fatty acid ester, and a serotonin receptor antagonist, and finally completed the present invention.

The present inventions are presented by the following aspects.
1. A patch containing a serotonin receptor antagonist, wherein the patch contains an adhesive layer comprising a non-functional acrylic adhesive, a water-soluble organic amine, a fatty acid ester, and a serotonin receptor antagonist as an active ingredient.
2. The patch containing a serotonin receptor antagonist according to the above 1, wherein the amount of the water-soluble organic amine is 1-10% by weight, and the amount of the fatty acid ester is 2-20% by weight.
3. The patch containing a serotonin receptor antagonist according to the above 1 or 2, wherein the serotonin receptor antagonist is selected from the group consisting of granisetron, ramosetron, palonosetron and ondansetron.
4. The patch containing a serotonin receptor antagonist according to any one of the above 1-3, wherein the serotonin receptor antagonist is granisetron, and the transdermal absorption delay time (lag time) is 5 hours or less.
5. The patch containing a serotonin receptor antagonist according to any one of the above 1-3, wherein the serotonin receptor antagonist is ramosetron, and the transdermal absorption delay time (lag time) is 6 hours or less.
6. The patch containing a serotonin receptor antagonist according to any one of the above 1-3, wherein the serotonin receptor antagonist is palonosetron, and the transdermal absorption delay time (lag time) is 5 hours or less.
7. The patch containing a serotonin receptor antagonist according to any one of the above 1-4, wherein the serotonin receptor antagonist is granisetron, and the time to maximum transdermal permeation rate is 12 hours or less.
8. The patch containing a serotonin receptor antagonist according to any one of the above 1-3 or 5, wherein the serotonin receptor antagonist is ramosetron, and the time to maximum transdermal permeation rate is 15 hours or less.
9. The patch containing a serotonin receptor antagonist according to any one of the above 1-3 or 6, wherein the serotonin receptor antagonist is palonosetron, and the time to maximum transdermal permeation rate is 10 hours or less.
10. The patch containing a serotonin receptor antagonist according to the above 4 or 7, wherein the transdermal permeation rate at 24 hours after application ($\mu g/cm^2/hr$)/maximum transdermal permeation rate ($\mu g/cm^2/hr$) is 0.6 or less.
11. The patch containing a serotonin receptor antagonist according to the above 6 or 9, wherein the transdermal permeation rate at 24 hours after application ($\mu g/cm^2/hr$)/maximum transdermal permeation rate ($\mu g/cm^2/hr$) is 0.5 or less.

Effect of the Invention

According to the present invention, by preparing a transdermal absorption-type patch containing an adhesive layer comprising a non-functional acrylic adhesive, a water-soluble organic amine, a fatty acid ester, and a serotonin receptor antagonist, a patch containing a serotonin receptor antagonist which can be administered once daily and repetitively can be provided. Said transdermal absorption-type patch enables a more efficient transdermal absorption of a serotonin receptor antagonist, shortens the transdermal absorption delay time (lag time), and achieves the maximum transdermal permeation rate of the drug within a short time, thereby achieves a rapid onset of drug efficacy and a rapid drug elimination from circulating blood. Therefore, said formulation enables an easy administration of the drug without causing pain and can improve the QOL of a patient.

MODE FOR CARRYING OUT THE INVENTION

One of the characteristics of the present invention is that a non-functional acrylic adhesive is mixed with a combination of a water-soluble organic amine and a fatty acid ester as absorption enhancers.

As an acrylic adhesive contained in an adhesive layer of a patch of the present invention, a non-functional adhesive which does not have a functional group such as a hydroxyl group, a carboxyl group, an amino group, or an epoxy group is preferable. If a functional group such as a carboxyl group or a hydroxyl group is present in an adhesive, problems such as decrease in drug release occur. Also, because said adhesive layer uses a water-soluble organic amine as an absorption enhancer, the presence of a functional group described above in the adhesive causes changes with time such as deterioration in the physical properties of the patch, which is not preferable.

An acrylic adhesive contained in an adhesive layer of a patch of the present invention may be, for example, a (meth)acrylic acid ester copolymer containing ethyl acrylate, butyl acrylate, 2-ethylhexyl acrylate, n-hexyl acrylate, or dodecyl acrylate etc. as the main monomer, and in particular, a copolymer containing 2-ethylhexyl acrylate is preferable.

Also, other than the main monomer, an acrylic acid ester copolymer containing vinyl acetate, N-vinylpyrrolidone, acrylonitrile, or styrene etc. can be used.

Namely, an acrylic adhesive suitable for a patch of the present invention may be, for example, an acrylic adhesive such as 2-ethylhexyl acrylate/2-ethylhexyl methacrylate/dodecyl methacrylate copolymer, 2-ethylhexyl acrylate/vinylpyrrolidone copolymer, 2-ethylhexyl acrylate/vinyl acetate copolymer, or methyl acrylate/2-ethylhexyl acrylate copolymer. Especially, 2-ethylhexyl acrylate/vinylpyrrolidone copolymer, 2-ethylhexyl acrylate/2-ethylhexyl methacrylate/dodecyl methacrylate copolymer and 2-ethylhexyl acrylate/vinyl acetate copolymer are preferable. The amount of an acrylic adhesive is 50% by weight to 95% by weight, and preferably 60% by weight to 90% by weight.

A water-soluble organic amine contained in an adhesive layer of a patch of the present invention functions as an absorption enhancer of a drug. A water-soluble organic amine may be, for example, monoethanolamine, diethanolamine, triethanolamine and diisopropanolamine, and in particular, diisopropanolamine is preferable. The amount of a water-soluble organic amine is 1% by weight to 10% by weight, and preferably 1.5% by weight to 7% by weight. When the amount of a water-soluble organic amine is more than 10% by weight, deterioration in the physical properties of an adhesive base occurs, and when the amount is less than 1% by weight, a high absorption enhancing effect cannot be achieved.

A fatty acid ester contained in an adhesive layer of a patch of the present invention is combined with a water-soluble organic amine to enhance the transdermal absorbability of a drug. A fatty acid ester may be, for example, isopropyl myristate, isopropyl palmitate, diethyl sebacate, diisopropyl adipate, cetyl 2-ethylhexanoate, diisopropyl sebacate, ethyl oleate, 2-hexyldecyl isostearate, myristyl myristate, cetyl palmitate, or isopropyl linoleate, and isopropyl myristate is preferable in view of compatibility with an adhesive and skin irritation. The amount of a fatty acid ester is 2% by weight to 20% by weight, and preferably 4% by weight to 16% by weight. When the amount of a fatty acid ester is more than 20% by weight, deterioration in the physical properties of an adhesive base occurs, and when the amount is less than 2% by weight, a high absorption enhancing effect cannot be achieved.

Also, in addition to the above absorption enhancer, a higher fatty acid may be contained in an adhesive layer. A higher fatty acid may be, for example, myristic acid, palmitic acid, stearic acid, isostearic acid, oleic acid, lauric acid, linoleic acid, or linolenic acid, and oleic acid is preferable. The amount of a higher fatty acid is 1% by weight to 10% by weight, and preferably 3% by weight to 7% by weight.

A serotonin receptor antagonist as an active ingredient contained in an adhesive layer of a patch of the present invention may be, for example, ramosetron, granisetron, palonosetron, ondansetron, azasetron, tropisetron, alosetron, or itasetron, which may be in its free base form or a salt form, or a mixture thereof. Preferred drugs are ondansetron, granisetron, palonosetron and ramosetron, and especially preferred are granisetron, palonosetron and ramosetron. The amount of a serotonin receptor antagonist in a transdermal absorption-type patch of the present invention is 1% by weight to 20% by weight, and preferably 1% by weight to 10% by weight. When the amount of a drug is less than 1% by weight, desirable drug efficacy cannot be achieved, and when the amount is more than 20% by weight, further improvement of the transdermal absorbability cannot be achieved, but rather the drug availability will decrease.

Also, an ingredient such as other absorption enhancer, an antioxidant, a plasticizer, or a surfactant can be appropriately contained in an adhesive layer in an appropriate amount if necessary.

As an absorption enhancer other than the above-mentioned ingredients, an alcohol such as propylene glycol, polyethylene glycol, 1,3-butanediol, oleyl alcohol, lauryl alcohol, or myristyl alcohol, a pyrrolidone derivative such as 1-pyrrolidone or N-methyl-2-pyrrolidone, a vegetable oil such as castor oil, olive oil, soybean oil, mentha oil, or sesame oil, crotamiton, dimethylsulfoxide, or L-menthol etc. can also be contained.

As an antioxidant, a tocopherol or a derivative thereof, ascorbic acid, ascorbyl stearate, dibutylhydroxytoluene, or butylhydroxyanisol etc. can be contained.

As a plasticizer, liquid paraffin, squalane, squalene, silicone oil, olive oil, castor oil, propylene glycol, polyethylene glycol, crotamiton, dimethylsulfoxide, diisopropyl adipate, diethyl sebacate, triethyl citrate, isostearic acid, or polyhydric alcohol fatty acid ester etc. can be contained.

As a surfactant, a generally-used surfactant in a transdermal absorption-type patch such as sorbitan fatty acid ester, glycerin fatty acid ester, polyglycerin fatty acid ester, polyoxyethylene sorbitan fatty acid ester, polyethylene glycol fatty acid ester, polyoxyethylene hydrogenated castor oil, or polyoxyethylene alkyl ether etc. can be contained.

A backing in a patch of the present invention is not especially limited if it does not affect the release of a drug and it is suitable for supporting an adhesive layer, and an elastic or non-elastic material can be used. For example, a film, a woven fabric, or a non-woven fabric composed of a synthetic resin such as polyurethane, polyester such as polyethylene terephthalate, polyvinyl acetate, polyvinyl chloride, polyethylene, or polypropylene etc. or a cotton material, or a composite material thereof can be used.

As a release liner covering a patch of the present invention, a plastic film used in a conventional patch can be used, and for example, a film having a thickness of 20-100 μm composed of polyethylene, polypropylene, polyester, or polyvinyl chloride etc. can be used. Also, in order to improve the peel property, a plastic film which is coated with a silicone resin or a fluorine resin etc. on the surface contacting with an adhesive layer can be used.

EXAMPLES

Hereinafter, the present invention is more specifically explained by means of Examples, but the present invention is not limited to these Examples.

Example 1

Diisopropanolamine and butylhydroxytoluene were dissolved in methanol, then isopropyl myristate and granisetron hydrochloride were added thereto, and the mixture was stirred until it became homogeneous. Further, to the mixture were added an acrylic adhesive and ethyl acetate solution, and stirred until it became homogeneous. Then, the mixture was spread on a silicone-treated surface of a release liner of polyester film having a thickness of 75 μm so that the thickness became homogeneous. The spread film was dried at 80° C. for about 10 minutes to remove the solvent, and an adhesive layer having a thickness of 75 μm was formed. Subsequently, a polyethylene terephthalate backing was bound to the adhesive layer to obtain a patch of the present invention. The amount of each ingredient is shown in Table 1.

Examples 2-13, and Comparative Examples 1-7 and Comparative Examples 11-12

According to each amount of ingredients in a base shown in Table 1 and Table 2, patches of each Example and each Comparative Example were prepared by the same manner as Example 1. Also, among the ingredients in a base, the adhesives used are shown in Table 3 in detail. The amount of each ingredient in the Tables is shown as % by weight.

Comparative Example 8

In reference to the formulation of Example 1 in Patent Document 1 [JP 2006-516601 A], a formulation of Comparative Example 8 was prepared according to each amount of ingredients in a base shown in Table 2.

Comparative Example 9

In reference to Example 1 (Formulation A) in Patent Document 2 [JP 2008-540662 A], a formulation of Comparative Example 9 was prepared according to each amount of ingredients in a base shown in Table 2.

Comparative Example 10

In reference to the formulation of Example 1 in Patent Document 3 [JP 2009-137925 A], a formulation of Comparative Example 10 was prepared according to each amount of ingredients in a base shown in Table 2.

TABLE 1

Formulas of Examples (Ex.) and Comparative Examples (Com.)

|  | Ex. 1 | Ex. 2 | Ex. 3 | Ex. 4 | Ex. 5 | Ex. 6 | Ex. 7 | Ex. 8 |
|---|---|---|---|---|---|---|---|---|
| Granisetron hydrochloride | 3.5 | 4 | 4 | 3 | 4 | 4 | 4 | 5 |
| Diisopropanolamine | 3 | 5 |  | 3 | 4 | 3 | 1.5 | 5 |
| Monoethanolamine |  |  | 2.5 |  |  |  |  |  |
| Isopropyl myristate | 5 | 5 | 5 | 5 | 5 | 5 | 5 | 5 |
| Propylene glycol |  |  |  |  |  |  |  |  |
| Acrylic adhesive A | 88 | 85.5 |  | 88.5 |  |  | 89.0 | 85 |
| Acrylic adhesive B |  |  | 88.5 |  | 87 | 88 |  |  |
| Acrylic adhesive C |  |  |  |  |  |  |  |  |
| Acrylic adhesive D |  |  |  |  |  |  |  |  |
| Acrylic adhesive E |  |  |  |  |  |  |  |  |
| Acrylic adhesive F |  |  |  |  |  |  |  |  |
| Butylhydroxytoluene | 0.5 | 0.5 |  | 0.5 |  |  | 0.5 |  |
| Total | 100 | 100 | 100 | 100 | 100 | 100 | 100 | 100 |
| Lag time (rat, hr) | 0.6 | 1.8 | 3.6 | 3.5 | 3.5 | 3.5 | 4.0 | 1.0 |
| Maximum transdermal permeation rate (rat, µg/cm$^2$/hr) | 22.6 | 21.5 | 11.6 | 13.9 | 10.2 | 9.9 | 7.6 | 35.1 |
| Time to maximum transdermal permeation rate (rat, hr) | 4.3 | 5.8 | 7.3 | 7.3 | 7.3 | 8.8 | 10.3 | 4.3 |
| Transdermal permeation rate at 24 hours (rat, µg/cm$^2$/hr) | 1.3 | 4.5 | 8.4 | 4.5 | 6.4 | 6.2 | 2.9 | 11.1 |
| Transdermal permeation rate at 24 hours (rat, µg/cm$^2$/hr)/Maximum transdermal permeation rate (rat, µg/cm$^2$/hr) | 0.06 | 0.21 | 0.72 | 0.32 | 0.63 | 0.63 | 0.38 | 0.32 |
| Lag time (human, hr) | 4.3 | 4.3 |  |  |  |  |  |  |
| Maximum transdermal permeation rate (human, µg/cm$^2$/hr) | 10.8 | 9.7 |  |  |  |  |  |  |
| Time to maximum transdermal permeation rate (human, hr) | 4.3 | 11.8 |  |  |  |  |  |  |

|  | Com. 1 | Com. 2 | Com. 3 | Com. 4 | Com. 5 | Com. 6 | Com. 7 |
|---|---|---|---|---|---|---|---|
| Granisetron hydrochloride | 4 | 4 | 5 | 5 | 5 | 4 | 4 |
| Diisopropanolamine |  |  | 5 | 5 | 5 |  |  |
| Monoethanolamine |  |  |  |  |  |  |  |
| Isopropyl myristate |  | 5 | 5 | 5 | 5 |  | 5 |
| Propylene glycol | 0.5 |  |  |  |  |  |  |
| Acrylic adhesive A |  | 90.5 |  |  |  |  |  |
| Acrylic adhesive B |  |  |  |  |  |  |  |
| Acrylic adhesive C |  |  |  |  |  | 96 | 91 |
| Acrylic adhesive D | 95.5 |  | 85 |  |  |  |  |
| Acrylic adhesive E |  |  |  | 85 |  |  |  |
| Acrylic adhesive F |  |  |  |  | 85 |  |  |
| Butylhydroxytoluene |  | 0.5 |  |  |  |  |  |
| Total | 100 | 100 | 100 | 100 | 100 | 100 | 100 |
| Lag time (rat, hr) | 10< | 4.6 | 2 | 2.2 | 2.2 | 5.8 | 5.3 |
| Maximum transdermal permeation rate (rat, µg/cm$^2$/hr) | 0.1 | 0.4 | 20.1 | 15.8 | 1.1 | 7.3 | 8.8 |
| Time to maximum transdermal permeation rate (rat, hr) | 10.3 | 20.8 | 5.8 | 5.8 | 23.8 | 19.3 | 11.8 |
| Transdermal permeation rate at 24 hours (rat, µg/cm$^2$/hr) | 0.03 | 0.4 | 10.5 | 8.7 | 1.1 | 6.4 | 8.7 |

TABLE 1-continued

Formulas of Examples (Ex.) and Comparative Examples (Com.)

| | | | | | | | |
|---|---|---|---|---|---|---|---|
| Transdermal permeation rate at 24 hours (rat, μg/cm²/hr)/Maximum transdermal permeation rate (rat, μg/cm²/hr) | 0.30 | 1.00 | 0.52 | 0.55 | 1.00 | 0.88 | 0.99 |
| Lag time (human, hr) | | | | | | | |
| Maximum transdermal permeation rate (human, μg/cm²/hr) | | | | | | | |
| Time to maximum transdermal permeation rate (human, hr) | | | | | | | |

TABLE 2

Formulas of Examples (Ex.) and Comparative Examples (Com.)

| | Ex. 9 | Ex. 10 | Com. 8 | Com. 9 | Com. 10 | Ex. 11 | Com. 11 | Ex. 12 | Ex. 13 | Com. 12 |
|---|---|---|---|---|---|---|---|---|---|---|
| Granisetron | 4 | 4 | 3 | 3.5 | | | | | | |
| Granisetron hydrochloride | | | | | 5 | | | | | |
| Ramosetron hydrochloride | | | | | | 6 | 6 | | | |
| Palonosetron hydrochloride | | | | | | | | 1 | 5 | 1 |
| Diisopropanolamine | 2 | 5 | | | | 6 | | 5 | 5 | 5 |
| Sodium hydroxide | | | | | 1 | | | | | |
| Isopropyl myristate | 5 | 5 | | 7.5 | 14 | 15 | | 5 | 5 | 5 |
| Lauric acid diethanolamide | | | | | 6.4 | | | | | |
| Oleic acid | | | | | | 6 | | | | |
| Acrylic adhesive A | | 85.5 | | | | | | 89 | 85 | |
| Acrylic adhesive B | | | | | 73.6 | 66 | 93 | | | |
| Acrylic adhesive C | 89 | | | | | | | | | |
| Acrylic adhesive D | | | | | | | | | | |
| Acrylic adhesive E | | | | | | | | | | |
| Acrylic adhesive F | | | | | | | | | | 89 |
| Acrylic adhesive (DURO-TAK 87-2287) | | | 97 | | | | | | | |
| Acrylic adhesive (DURO-TAK 87-6173) | | | | 89 | | | | | | |
| Butylhydroxytoluene | | 0.5 | | | | 1 | 1 | | | |
| Total | 100 | 100 | 100 | 100 | 100 | 100 | 100 | 100 | 100 | 100 |
| Lag time (rat, hr) | 4.4 | 3.6 | 4.2 | 3.7 | 4.3 | 5.5 | 10< | 3.0 | 2.7 | 2.4 |
| Maximum transdermal permeation rate (rat, μg/cm²/hr) | 11.4 | 16.1 | 4.8 | 6.9 | 14.8 | 4.1 | 1.4 | 5.3 | 27.6 | 0.06 |
| Time to maximum transdermal permeation rate (rat, hr) | 10.3 | 8.8 | 23.8 | 20.8 | 11.8 | 12.8 | 24.8 | 7.3 | 5.8 | 19.3 |
| Transdermal permeation rate at 24 hours (rat, μg/cm²/hr) | 10.1 | 6.3 | 4.8 | 6.8 | 11.2 | 4.1 | 1.4 | 0.9 | 11.9 | 0.03 |
| Transdermal permeation rate at 24 hours (rat, μg/cm²/hr)/Maximum transdermal permeation rate (rat, μg/cm²/hr) | 0.89 | 0.39 | 1.00 | 0.99 | 0.76 | 1.00 | 1.00 | 0.17 | 0.43 | 0.50 |

Each component of the acrylic adhesives A-F in the above Tables showing the formula list and the functional group thereof are shown in the Table 3 below.

TABLE 3

| | Functional group | Component |
|---|---|---|
| Acrylic adhesive A | no | 2-ethylhexyl acrylate/2-ethylhexyl methacrylate/dodecyl methacrylate copolymer solution |
| Acrylic adhesive B | no | 2-ethylhexyl acrylate/vinylpyrrolidone copolymer solution |
| Acrylic adhesive C | no | 2-ethylhexyl acrylate/vinyl acetate copolymer solution |
| Acrylic adhesive D | OH | 2-ethylhexyl acrylate/vinyl acetate/2-hydroxyethyl acrylate copolymer solution |
| Acrylic adhesive E | OH | 2-ethylhexyl acrylate/vinyl acetate/2-hydroxyethyl acrylate copolymer solution |
| Acrylic adhesive F | COOH | 2-ethylhexyl acrylate/vinyl acetate/acrylic acid copolymer solution |

Test Example 1

Rat Transdermal Permeation Test

In order to study the release of an active ingredient from each formulation of Examples and Comparative Examples, in vitro rat transdermal permeation test was carried out using a hairless rat.

An abdominal skin of a hairless rat of 8-10 weeks old (body weight: 200-300 g) was peeled, and set on a Franz diffusion cell (opening area: 1.77 cm$^2$) with the dermal side facing the receptor layer side, and warm water at 37° C. was circulated in the circumference of the cell. Then, each patch was applied to the horny layer side of the skin. A PBS (pH 7.4) solution was used as receptor solution which was sampled every 90 minutes at the rate of 3 ml/hr, and the drug concentration in the sample was measured by a high-performance liquid chromatographic method. Also, based on the obtained results, parameters such as lag time (hr), transdermal permeation rate (flux: μg/cm$^2$/hr), and maximum transdermal permeation rate were calculated. In addition, based on the transdermal permeation rate at 24 hours after application, the parameter "transdermal permeation rate at 24 hours after application (μg/cm$^2$/hr)/maximum transdermal permeation rate (μg/cm$^2$/hr)" was calculated. Said parameter is an indicator of drug elimination rate from circulating blood. The smaller said parameter of a formulation is, the more rapidly a drug in the formulation disappears from circulating blood, which is preferable as a formulation of the present invention.

Figure 1:
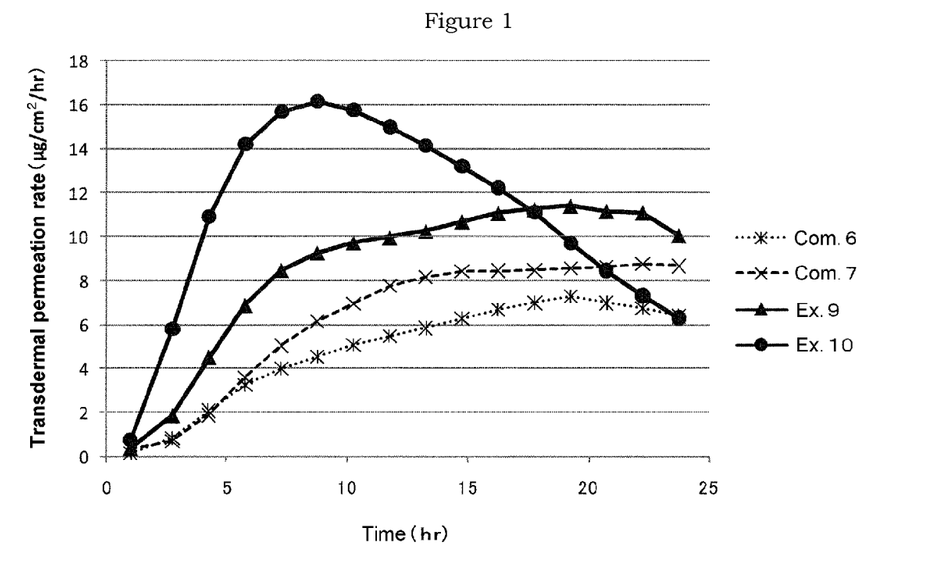
FIG. 1 shows the result of in vitro rat transdermal permeation test in Test Example 1.

Each parameter calculated from the test results is shown in Table 1 and Table 2. Also, a graph of the transdermal permeation rate (μg/cm$^2$/hr) of the formulations in Examples 9-10 and Comparative Examples 6-7 is shown in FIG. 1.

Test Example 2

Human Transdermal Permeation Test

Regarding each formulation of Example 1 and Example 2, in vitro human transdermal permeation test was carried out.

Figure 2:
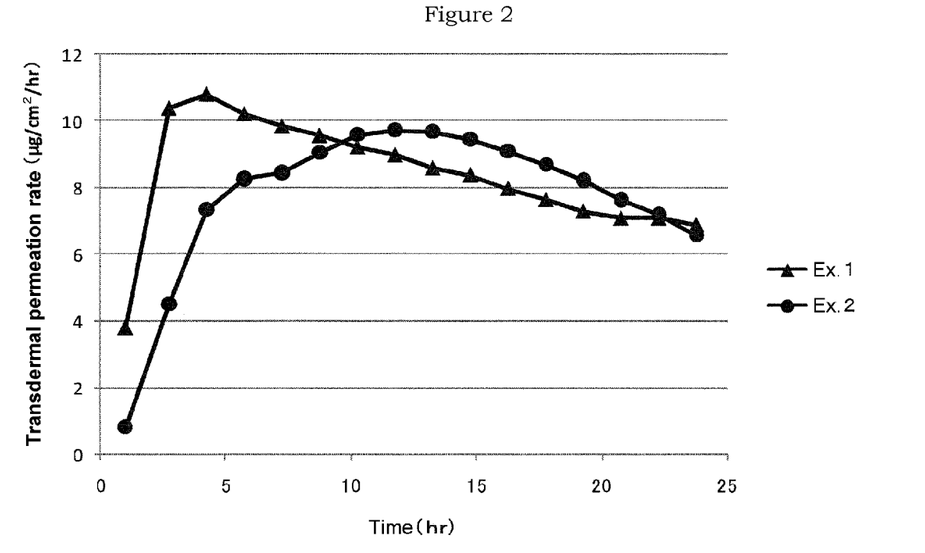
FIG. 2 shows the result of in vitro human transdermal permeation test in Test Example 2.

A cryopreserved human skin was thawed, cut into an about 750 μm of dermatome, and then set on a Franz diffusion cell (opening area: 1.77 cm$^2$) with the dermal side facing the receptor layer side, and warm water at 37° C. was circulated in the circumference of the cell. Subsequently, each patch was applied to the horny layer side of the skin. A PBS (pH 7.4) solution was used as receptor solution which was sampled every 90 minutes at the rate of 3 ml/hr, and the drug concentration in the sample was measured by a high-performance liquid chromatographic method. Also, based on the obtained results, the transdermal permeation rate per unit time and unit area (μg/cm$^2$/hr) etc. was calculated. The results are shown in Table 1 and FIG. 2.

Test Example 3

Stability Test (Observation of Property and Crystal Deposition)

Regarding a sample of each formulation in Example 8 and Comparative Examples 3-5, the stability of the formulation preserved for 1 year at room temperature was investigated. The property (color) and crystal deposition of each formulation were visually observed before and after preservation. The results are shown in Table 4.

TABLE 4

| | | Sample | | | |
|---|---|---|---|---|---|
| Test item | | Example 8 | Comparative Example 3 | Comparative Example 4 | Comparative Example 5 |
| Property (color) | before preservation | clear and colorless | clear and colorless | light brown | light milky white |
| | after preservation | clear and colorless | light milky white | dark brown | milky white |
| Crystal deposition | before preservation | no | no | no | yes |
| | after preservation | no | yes | yes | yes |

[Discussion]

Granisetron (Hydrochloride)-Containing Patch

The results of in vitro rat transdermal permeation tests shown in Table 1 and Table 2 demonstrate that each formulation of Examples 1-10 of the present invention containing granisetron (hydrochloride) as a drug showed a short lag time (5 hours or less), a short time to maximum transdermal permeation rate (12 hours or less), and a high maximum transdermal permeation rate. Thus, it was proved that said patch of the present invention could rapidly release the drug and thus could show a drug release sufficient for the treatment. Meanwhile, it was proved that each formulation of Comparative Examples 1-10 had a significantly lower maximum transdermal permeation rate compared to each formulation of Examples having the same drug concentration. Also, regarding each formulation of Comparative Examples 1 and 6-7, the lag time was more than 5 hours, which was longer than the lag time of each formulation of Examples. Further, regarding each formulation of Comparative Examples 2, 5-6 and 8-9, the time to maximum transdermal permeation rate was far more than 12 hours, which was significantly longer than each formulation of Examples. Therefore, these formulations of Comparative Examples were proved to be inferior to each formulation of Examples in rapid drug release. Moreover, as shown in Table 4, each formulation of Comparative Example 3 and Comparative Example 4 had a possibility of crystallization of a drug during a long-term preservation and thus was proved to be far inferior to each formulation of Examples in stability.

In addition, regarding the parameter "transdermal permeation rate at 24 hours (μg/cm$^2$/hr)/maximum transdermal permeation rate (μg/cm$^2$/hr)" which is a parameter of drug elimination rate from circulating blood, each formulation of Examples 1-2, 4, 7-8 and 10 had a value of 0.6 or less, and thus was confirmed to be a formulation which could achieve a rapid drug elimination from circulating blood.

Meanwhile, regarding each formulation of Comparative Examples except for the formulation of Comparative Example 1 which is significantly inferior in lag time and maximum transdermal permeation rate and the formulations of Comparative Example 3 and Comparative Example 4 which are inferior in drug stability during preservation, the parameter "transdermal permeation rate at 24 hours ($\mu g/cm^2/hr$)/maximum transdermal permeation rate ($\mu g/cm^2/hr$)" was 0.7 or more, and thus was proved to be slow in drug elimination from circulating blood.

Also, in the results of in vitro human transdermal permeation test using granisetron (hydrochloride)-containing patch of the present invention as the test formulation, the granisetron-containing formulation of the present invention showed a short lag time (5 hours or less) and a short time to maximum transdermal permeation rate (12 hours or less). Accordingly, a patch of the present invention was demonstrated to show a rapid onset of drug efficacy.

meation rate ($\mu g/cm^2/hr$)" which is a parameter of drug elimination rate from circulating blood, each formulation had a value of 0.5 or less, and thus was confirmed to be a formulation which could achieve a rapid drug elimination from circulating blood.

Meanwhile, regarding the formulation of Comparative Example 12, the maximum transdermal permeation rate was very low, and the time to maximum transdermal permeation rate was far more than 10 hours. Therefore, the formulation of Comparative Example 12 was proved to be significantly inferior as compared to the formulation of Example 12 having the same drug concentration.

Additional specific Formulation Examples (Form.) of a patch of the present invention are shown in Table 5 below.

The amount of each ingredient in the Table is shown as % by weight.

TABLE 5

|  | Form. 1 | Form. 2 | Form. 3 | Form. 4 | Form. 5 | Form. 6 | Form. 7 |
|---|---|---|---|---|---|---|---|
| Ramosetron hydrochloride | 6 | 8 | 10 |  |  |  |  |
| Ondansetron |  |  |  | 3 | 6 |  |  |
| Ondansetron hydrochloride |  |  |  |  |  | 3 | 4 |
| Diisopropanolamine | 3 | 5 | 6 |  |  | 5 |  |
| Monoethanolamine |  |  |  |  |  |  | 4 |
| Triethanolamine |  |  |  | 3 | 6 |  |  |
| Isopropyl myristate | 15 | 10 | 5 |  |  |  |  |
| Diethyl sebacate |  |  |  | 4 | 4 | 4 | 4 |
| Isostearic acid | 6 |  |  |  |  |  |  |
| Lactic acid |  | 2 |  | 1 |  |  | 3 |
| Oleic acid |  |  | 6 | 2 | 3 |  |  |
| Propylene glycol |  |  |  |  |  |  | 3 |
| Polyethylene glycol |  |  |  |  |  | 9 |  |
| N-methyl-2-pyrrolidone |  |  |  | 5 |  |  |  |
| Acrylic adhesive A* |  |  |  | 82 | 81 | 79 | 82 |
| Acrylic adhesive B* | 69 | 74 | 72 |  |  |  |  |
| Butylhydroxytoluene | 1.0 | 1.0 | 1.0 |  |  |  |  |
| Total | 100 | 100 | 100 | 100 | 100 | 100 | 100 |

*see Table 3

Ramosetron Hydrochloride-Containing Patch

The results of in vitro rat transdermal permeation test shown in Table 2 demonstrate that the formulation of Example 11 containing ramosetron hydrochloride as a drug showed a short lag time (6 hours or less), a short time to maximum transdermal permeation rate (15 hours or less), and a high maximum transdermal permeation rate. Thus, it was proved that said patch could rapidly release the drug and thus could show a drug release sufficient for the treatment. Meanwhile, regarding the formulation of Comparative Example 11 containing the same amount of ramosetron hydrochloride as the formulation of Example 11, the lag time was more than 10 hours, and the maximum transdermal permeation rate was low. Therefore, the formulation of Comparative Example 11 was proved to be significantly inferior to the formulation of Example 11.

Palonosetron Hydrochloride-Containing Patch

The results of in vitro rat transdermal permeation test shown in Table 2 demonstrate that each formulations of Examples 12 and 13 containing palonosetron hydrochloride as a drug showed a short lag time (5 hours or less), a short time to maximum transdermal permeation rate (10 hours or less), and a high maximum transdermal permeation rate. Thus, it was proved that said patch could rapidly release the drug and thus could show a drug release sufficient for the treatment.

In addition, regarding the parameter "transdermal permeation rate at 24 hours ($\mu g/cm^2/hr$)/maximum transdermal per- Industrial Applicability The present invention can achieve a more efficient and continuous transdermal absorption of a serotonin receptor antagonist, shorten the transdermal absorption delay time (lag time) and the time to maximum transdermal permeation rate resulting in a rapid onset of drug efficacy, and further achieve a rapid drug elimination from circulating blood, and thus can provide a novel patch containing a serotonin receptor antagonist which can be administered once daily and repetitively.

The invention claimed is:

1. A patch containing a serotonin receptor antagonist, wherein the patch contains an adhesive layer comprising a non-functional acrylic adhesive, 1-10% by weight of a water-soluble organic amine, 2-20% by weight of a fatty acid ester, and a serotonin receptor antagonist as an active ingredient wherein the patch does not contain lauric acid diethanolamide.

2. The patch containing a serotonin receptor antagonist according to claim 1, wherein the serotonin receptor antagonist is selected from the group consisting of granisetron, ramosetron, palonosetron and ondansetron, and a salt thereof, and a mixture thereof.

3. The patch containing a serotonin receptor antagonist according to claim 1, wherein the serotonin receptor antagonist is granisetron, or a salt thereof, and the transdermal absorption delay time (lag time) is 5 hours or less.

4. The patch containing a serotonin receptor antagonist according to claim 1, wherein the serotonin receptor antagonist is ramosetron, or a salt thereof, and the transdermal absorption delay time (lag time) is 6 hours or less.

5. The patch containing a serotonin receptor antagonist according to claim 1, wherein the serotonin receptor antagonist is palonosetron, or a salt thereof, and the transdermal absorption delay time (lag time) is 5 hours or less.

6. The patch containing a serotonin receptor antagonist according to claim 1, wherein the serotonin receptor antagonist is granisetron, or a salt thereof, and the time to maximum transdermal permeation rate is 12 hours or less.

7. The patch containing a serotonin receptor antagonist according to claim 1, wherein the serotonin receptor antagonist is ramosetron, or a salt thereof, and the time to maximum transdermal permeation rate is 15 hours or less.

8. The patch containing a serotonin receptor antagonist according to claim 1, wherein the serotonin receptor antagonist is palonosetron, or a salt thereof, and the time to maximum transdermal permeation rate is 10 hours or less.

9. The patch containing a serotonin receptor antagonist according to claim 3, wherein the transdermal permeation rate at 24 hours after application ($\mu g/cm^2/hr$)/maximum transdermal permeation rate ($\mu g/cm^2/hr$) is 0.6 or less.

10. The patch containing a serotonin receptor antagonist according to claim 5, wherein the transdermal permeation rate at 24 hours after application ($\mu g/cm^2/hr$)/maximum transdermal permeation rate ($\mu g/cm^2/hr$) is 0.5 or less.

\* \* \* \* \*